United States Patent
Chang et al.

(10) Patent No.: US 8,710,291 B2
(45) Date of Patent: Apr. 29, 2014

(54) TRANSLUCENT INTERNAL GRAPHICS ENHANCEMENT

(75) Inventors: Sharon S. Chang, Alpharetta, GA (US); Darold D. Tippey, Brunswick, GA (US); Shirlee Ann Weber, Neenah, WI (US); Jessica Sara Van Handel, Menasha, WI (US); Vasily A. Topolkaraev, Appleton, WI (US); Debra Ann Miller, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1373 days.

(21) Appl. No.: 11/966,392

(22) Filed: Dec. 28, 2007

(65) Prior Publication Data

US 2009/0171307 A1 Jul. 2, 2009

(51) Int. Cl.
*A61F 13/42* (2006.01)

(52) U.S. Cl.
USPC .......................................................... 604/361

(58) Field of Classification Search
USPC ......................................... 604/358, 361, 378
See application file for complete search history.

(56) References Cited

U.S. PATENT DOCUMENTS

| | | | |
|---|---|---|---|
| 2,249,867 A | 7/1941 | Snelling | |
| 4,022,211 A | 5/1977 | Timmons et al. | |
| 4,276,340 A * | 6/1981 | de Leiris | 428/166 |
| 4,798,603 A | 1/1989 | Meyer et al. | |
| 5,089,548 A | 2/1992 | Zimmel et al. | |
| 5,167,652 A | 12/1992 | Mueller | |
| 5,176,668 A | 1/1993 | Bernardin | |
| 5,176,672 A | 1/1993 | Bruemmer et al. | |
| 5,192,606 A | 3/1993 | Proxmire et al. | |
| 5,354,289 A | 10/1994 | Mitchell et al. | |
| 5,509,915 A | 4/1996 | Hanson et al. | |
| 5,690,624 A | 11/1997 | Sasaki et al. | |
| 5,766,212 A | 6/1998 | Jitoe et al. | |
| 5,843,056 A | 12/1998 | Good et al. | |
| 5,855,999 A | 1/1999 | McCormack et al. | |
| 5,879,341 A | 3/1999 | Odorzynski et al. | |
| 5,947,943 A | 9/1999 | Lee | |
| 6,075,178 A | 6/2000 | La Wilhelm et al. | |
| 6,908,648 B2 * | 6/2005 | Kasahara | 428/32.25 |
| 7,154,019 B2 | 12/2006 | Mishima et al. | |
| 7,169,137 B2 | 1/2007 | Shimada | |
| 7,205,041 B2 | 4/2007 | Nair et al. | |
| 2001/0031954 A1 | 10/2001 | Jordan et al. | |
| 2002/0007162 A1 | 1/2002 | Cammarota et al. | |
| 2005/0234414 A1 * | 10/2005 | Liu | 604/361 |
| 2006/0020249 A1 | 1/2006 | Allen | |

FOREIGN PATENT DOCUMENTS

| | | |
|---|---|---|
| EP | 0925769 | 6/1999 |
| JP | 10085257 | 4/1998 |
| JP | 2001170106 A | 6/2001 |
| JP | 2002-369840 | 12/2002 |
| WO | 2005102239 A1 | 11/2005 |
| WO | WO 2006/128665 | 12/2006 |

OTHER PUBLICATIONS

International Search Report and Written Opinion, PCT/IB2008/055516, 10 pages (Aug. 17, 2009).
Extended European Search Report from EP Patent Application No. 08866394.3 mailed Feb. 2, 2012.
Patent Examination Report for Australian Patent Application No. 2008345262 dated Feb. 14, 2013; 4 pages.

* cited by examiner

*Primary Examiner* — Susan Su
(74) *Attorney, Agent, or Firm* — Armstrong Teasdale LLP

(57) ABSTRACT

Methods for forming a translucent window on the inner surface of a liquid impermeable breathable film outer cover of an absorbent product, such as a diaper, for viewing a water dispersible ink to indicate when an insult has occurred are disclosed. Additionally, absorbent products having a translucent window and a water dispersible ink are disclosed.

15 Claims, 2 Drawing Sheets

TRANSLUCENT INTERNAL GRAPHICS ENHANCEMENT

BACKGROUND OF DISCLOSURE

The present disclosure generally relates to forming a translucent window on a liquid impermeable material for viewing a fading graphic. More specifically, the present disclosure is directed to forming a translucent window on the inner surface of a liquid impermeable breathable film outer cover of an absorbent product, such as a diaper, for viewing a water dispersible ink to indicate when an insult has occurred.

Typical of disposable absorbent products are disposable infant diapers and disposable incontinent pads for adult patients. During the use of such disposable diapers and incontinent pads, disposable absorbent products become wet and require replacement to ensure adequate humane care of the infant and adult patients. In the past, the wetness of the products was monitored manually by either the visual or tactile inspection of the internal absorbent materials held within the impervious film-outer cover. Such an inspection can be time consuming and often can be unpleasant.

In view of the nature of visual or tactile inspections of the disposable absorbent products, development of moisture indicators that either change from colorless to colored or change from one color to another color in the presence of moisture were developed. Additionally, there have been products in which messages or graphics are printed onto the outer cover and once wetted, the messages or graphics fade to indicate the presence of moisture.

Many consumers have complained that it is difficult with current fading indicators to distinguish when the message, graphic, or color fades at night or in darker rooms as it is difficult to see through the outer covers of conventional absorbent products. As such, there is a need for an absorbent product having a translucent window formed on the inner surface of the liquid impermeable outer cover to allow for a more visible, noticeable change with a wetness indicator.

SUMMARY OF THE DISCLOSURE

It has been found that a translucent window for viewing fading graphics can be formed using a clearing composition and a water dispersible ink. Specifically, the translucent window is formed by first applying a clearing composition to the inner surface of a liquid impermeable outer cover and then applying a water dispersible ink over the clearing composition. In one embodiment, the clearing composition is a clearing varnish. In another embodiment, the clearing composition is a paraffin wax.

As such, the present disclosure is directed to an absorbent product comprising a liquid impermeable outer cover comprising a clearing varnish capable of forming a translucent window and a water dispersible ink applied over the translucent window; an absorbent material; and a liquid permeable inner layer. The clearing varnish has at least one of a number average molecular weight of from about 150 to about 1500, a melting point of from about 65° C. to about 95° C., and a melt index of from about 300 to about 1500.

The present disclosure is further directed to an absorbent product comprising a liquid impermeable outer cover comprising a clearing varnish capable of forming a translucent window and a water dispersible ink applied over the translucent window; an absorbent material; and a liquid permeable inner layer. The clearing varnish is selected from the group consisting of an epoxidized soybean oil, an ethylene-vinyl acetate copolymer, a tallow-based oleamide, a polyethylene glycol distearate, and combinations thereof. The water dispersible ink comprises isopropyl alcohol, methyl alcohol, and an organic volatile.

The present disclosure is further directed to an absorbent product comprising a liquid impermeable outer cover; an absorbent material; and a liquid permeable inner layer. The liquid impermeable outer cover comprises a paraffin wax and a water dispersible ink applied over the paraffin wax.

The present disclosure is further directed to a method of making an absorbent product comprising a translucent window for viewing a fading graphic. The method comprises: applying a clearing varnish onto an inner surface of a liquid impermeable outer cover to form a translucent window; and printing a water dispersible ink over the translucent window. The clearing varnish has at least one of a number average molecular weight of from about 150 to about 1500, a melting point of from about 65° C. to about 95° C., and a melt index of from about 300 to about 1500.

The present disclosure is further directed to a method of making an absorbent product comprising a fading graphic. The method comprises: heating a paraffin wax; applying the paraffin wax onto an inner surface of a liquid impermeable outer cover to form a translucent window; and printing a water dispersible ink over the translucent window.

Other objects and features will be in part apparent and in part pointed out hereinafter.

BRIEF DESCRIPTION OF THE DRAWINGS

Corresponding reference characters indicate corresponding parts throughout the drawings.

Definitions

Within the context of this specification, each term or phrase below includes the following meaning or meanings:

As used herein, "number average molecular weight" is a way of measuring the molecular weight of a polymer. Specifically, "number average molecular weight" refers to the average of the molecular weights of the individual polymers. It is determined by measuring the molecular weight of all of the molecules, summing the weights, and dividing by the number of molecules.

As used herein, "melt index" refers to the amount, in grams, of a thermoplastic material which can be forced through an extrusion rheometer orifice under the conditions as set forth in the standardized test method of ASTM D1238.

These terms may be defined with additional language in the remaining portions of the specification.

DETAILED DESCRIPTION OF THE DISCLOSURE

The present disclosure is generally related to forming a translucent window on the inner surface of a liquid impermeable breathable film outer cover of an absorbent product for viewing a water dispersible ink to indicate when an insult has occurred. For example, in one embodiment, the absorbent product has at least one graphic image on the inner surface of the outer cover when dry. Once the absorbent product is wetted, however, the graphic image begins fading to indicate that the product has become wet. With the translucent window produced in the present disclosure, the fading graphic image is more easily seen on the outer cover.

While described herein in terms of forming a translucent window on an absorbent product such as a diaper for use as a wetness indicator, it should be recognized by one skilled in the art that the translucent window can be formed on any suitable personal care product for use as one of various types of indicators. For example, the translucent window can be used on one or more personal care products to indicate the condition of the product, a condition of the user, and the like.

The present disclosure is primarily described herein in combination with an absorbent disposable diaper. It is readily apparent to one skilled in the art based on the disclosure herein, however, that the translucent window and inks described herein can also be used in combination with numerous other disposable absorbent products such as, for example, training pants, adult incontinence garments, feminine napkins, and the like.

Figure 1:
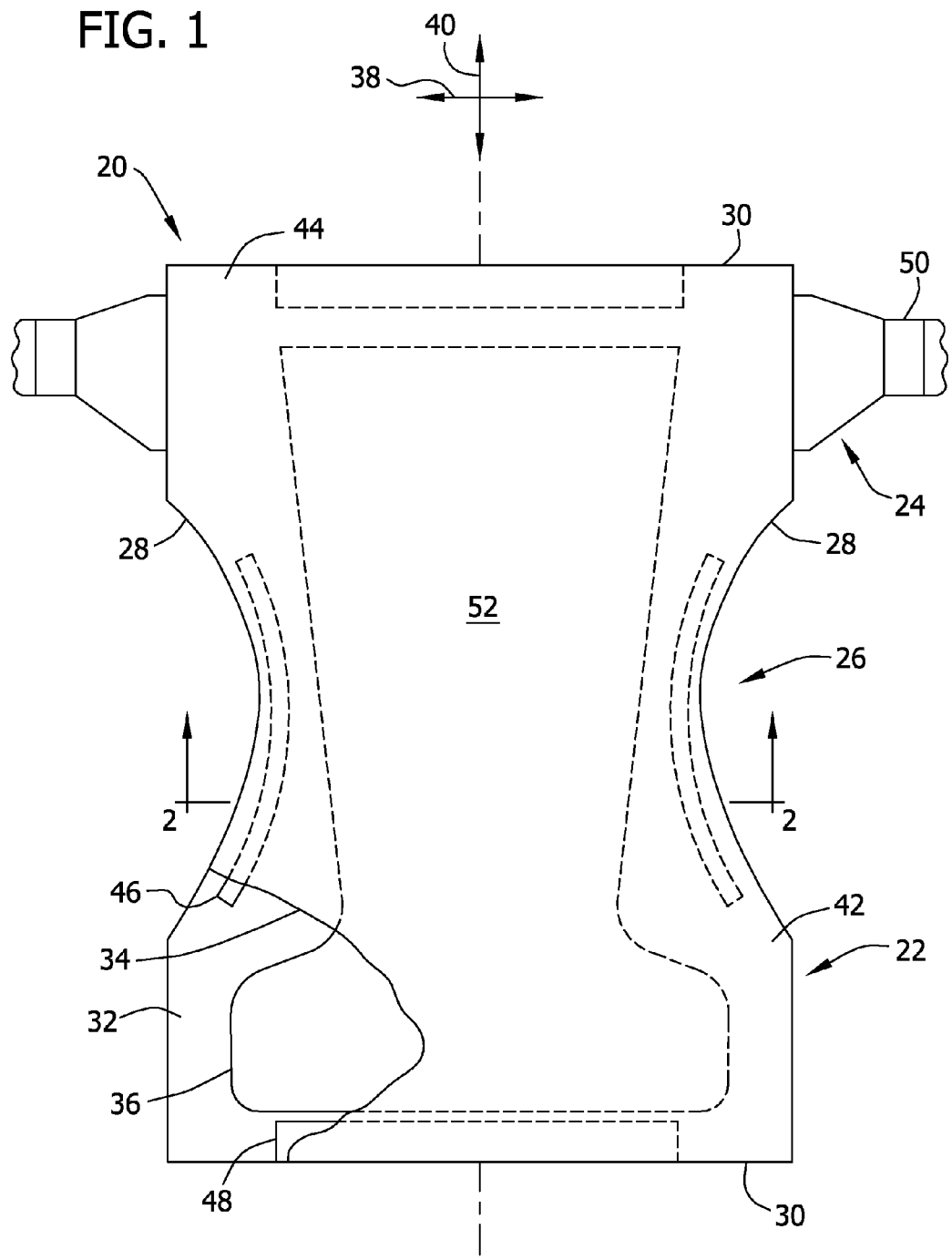
FIG. 1 representatively shows a partially cut away top plan view of an absorbent product in a stretched and laid flat condition with the surface of the product which contacts the skin of the wearer facing the viewer.
Figure 2:
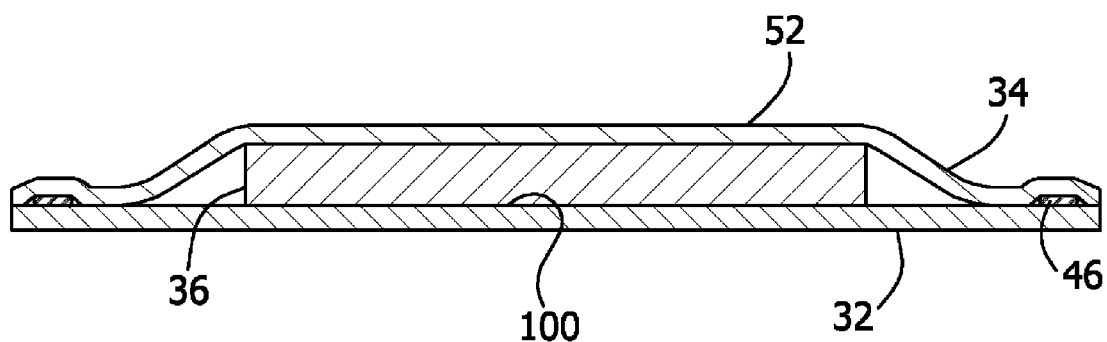
FIG. 2 representatively shows a sectional view of the absorbent product of FIG. 1 taken along line 2-2.

With reference to FIGS. 1 and 2, an integral absorbent product, such as a disposable diaper 20, generally defines a front waist section 22, a rear waist section 24, an intermediate section 26 which interconnects the front and rear waist section, a pair of laterally opposed side edges 28, and a pair of longitudinally opposed end edges 30. The front and rear waist sections include the general portions of the product which are constructed to extend substantially over the wearer's front and rear abdominal regions, respectively, during use. The intermediate section of the product includes the general portion of the product, which is constructed to extend through the wearer's crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

FIG. 1 is a representative plan view of the diaper 20 in a flat, non-contracted state. Portions of the structure are partially cut away to more clearly show the interior construction of the diaper 20, and the surface of the diaper which contacts the wearer is facing the viewer. The diaper 20 includes a substantially liquid impermeable outer cover 32, a porous, liquid permeable inner liner 34 positioned in facing relation with the outer cover 32, and an absorbent material 36, such as an absorbent pad, which is located between the outer cover and the inner liner. The diaper 20 also defines a lateral direction 38 and a longitudinal direction 40. Marginal portions of the diaper 20, such as marginal sections of the outer cover 32, may extend past the terminal edges of the absorbent material 36. In the illustrated embodiment, for example, the outer cover 32 extends outwardly beyond the terminal marginal edges of the absorbent material 36 to form side margins 42 and end margins 44 of the diaper 20. The inner liner 34 is generally coextensive with the outer cover 32, but may optionally cover an area which is larger or smaller than the area of the outer cover 32, as desired.

To provide improved fit and to help reduce leakage of body exudates from the diaper 20, the side margins 42 and end margins 44 of the diaper may be elasticized with suitable elastic members, such as leg elastic members 46 and waist elastic members 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 48 can be employed to elasticize the end margins 44 of the diaper 20 to provide elasticized waistbands. The waist elastics are configured to operably gather and shirr the waistband sections to provide a resilient, comfortably close fit around the waist of the wearer.

The elastic members 46 and 48 are secured to the diaper 20 in an elastically contractible condition so that in a normal under strain configuration, the elastic members effectively contract against the diaper 20. For example, the elastic members 46 and 48 may be elongated and secured to the diaper 20 while the diaper is in an uncontracted condition. In FIGS. 1 and 2, the elastic members 46 and 48 are illustrated in their uncontracted, stretched condition for the purpose of clarity. The diaper 20 may also include a pair of elasticized, longitudinally extending containment flaps (not shown), which are configured to maintain an upright, perpendicular arrangement in at least the intermediate section 26 of the diaper 20 to serve as an additional barrier to the lateral flow of body exudates. Suitable constructions and arrangements of containment flaps are well known to those skilled in the art.

Alternatively, the diaper 20 may include a pair of separate, elasticized and gathered leg gussets (not shown) or combination leg gussets/containment flaps (not shown) which are attached to the diaper along the side margins 42 in at least the intermediate section 26 of the diaper 20 to provide elasticized leg cuffs. Such gussets or combination gussets/containment flaps may be configured to extend beyond and bridge across the respective concave portion of the side margins 42.

The diaper 20, as representatively illustrated in FIGS. 1 and 2, may further include a pair of fasteners 50 employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member can be associated with each fastener and may be constructed to be nonelasticized, or to be elastically stretchable at least along the lateral direction 38 of diaper 20.

The diaper may further include a surge management layer (not shown) positioned between the inner liner 34 and the absorbent material 36 which is configured to efficiently hold and distribute liquid exudates to the absorbent material 36. The surge management layer can prevent the liquid exudates from pooling and collecting on the portion of the diaper positioned against the wearer's skin, thereby reducing the level of skin hydration. Suitable constructions and arrangements of surge management layers are well known to those skilled in the art. Other suitable diaper components may also be incorporated on absorbent products described herein.

The diaper 20 may be of various suitable shapes. For example, the diaper may have an overall rectangular shape, T-shape, or an approximately hour-glass shape. In the shown embodiment, the diaper 20 is I-shaped. Examples of diaper configurations suitable for use in connection with the instant application and other diaper components suitable for use on diaper 20 are described in U.S. Pat. No. 4,798,603 issued Jan. 17, 1989 to Meyer et al.; U.S. Pat. No. 5,176,668 issued Jan. 5, 1993, to Bernardin; U.S. Pat. No. 5,176,672 issued Jan. 5, 1993 to Bruemmer et al.; U.S. Pat. No. 5,192,606 issued Mar. 9, 1993 to Proxmire et al.; and U.S. Pat. No. 5,509,915 issued Apr. 23, 1996 to Hanson et al., the disclosures of which are hereby incorporated by reference to the extent they are consistent herewith. The various aspects and configurations of the disclosure can provide distinctive combinations of softness, body conformity, reduced red-marking of the wearer's skin, reduced hydration, and improved containment of body exudates.

The various components of the diaper 20 are integrally assembled together employing various types of suitable attachment means, such as adhesive, sonic bonds, thermal bonds, or combinations thereof. In the shown embodiment, for example, the inner liner 34 and the outer cover 32 are assembled to each other and to the absorbent material 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 46 and 48 and the fasteners 50, may be assembled into the diaper 20 by employing the above-identified attachment mechanisms.

The outer cover 32 of the diaper 20, as representatively illustrated in FIGS. 1 and 2, may suitably be composed of material which is either liquid permeable or liquid impermeable. It is generally preferred that the outer cover 32 be formed from a material which is substantially impermeable to liquids. For example, a typical outer cover can be manufactured from a thin plastic film or other flexible liquid-impermeable material. For example, the outer cover 32 may be formed from a polyethylene film having a thickness of from about 0.012 millimeter (0.5 mil) to about 0.051 millimeter (2.0 mils). If it is desired to present the outer cover with a more clothlike feeling, the outer cover 32 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mils) may have thermally laminated thereto a spunbond web of polypropylene fibers, which fibers have a denier of about 1.5 to 2.5 per filament, which nonwoven web has a basis weight of about 17 grams per square meter (0.5 ounce per square yard). Methods of forming such clothlike outer covers are known to those skilled in the art. Further, the outer cover 32 may be formed of a woven or nonwoven fibrous web layer which has been totally or partially constructed or treated to impart a desired level of liquid impermeability to selected regions that are adjacent or proximate to the absorbent material 36.

Desirably, the outer cover 32 may be composed of a "breathable" material which permits vapors to escape from the absorbent material 36 while still preventing liquid exudates from passing through the outer cover 32. For example, the outer cover 20 is desirably constructed to be permeable to at least water vapor and has a water vapor transmission rate of at least about 1000 g/m$^2$/24 hours, desirably at least about 1500 g/m$^2$/24 hours, more desirably at least about 2000 g/m$^2$/24 hours, and even more desirably at least about 3000 g/m$^2$/24 hours. Materials which have a water vapor transmission rate less than those above do not allow a sufficient amount of air exchange and undesirably result in increased levels of skin hydration. As used herein, the phrase "water vapor transmission rate" (WVTR) refers to the WVTR value according to the Water Vapor Transmission Rate Test which is described in further detail herein below.

In a particular embodiment, the outer cover 20 is provided by a microporous film/nonwoven laminate material comprising a spunbond nonwoven material laminated to a microporous film. For example, the laminate may include a 0.6 osy (20.4 gsm) polypropylene spunbond material thermally attached to a 18.7 gsm stretched microporous film. The film may include from about 20 percent to about 75 percent by weight calcium carbonate particulates and the remainder primarily low density polyethylene. The film is then stretched which causes the polyethylene component to stretch while the particulates remain unstretched, thus causing voids to develop around the calcium carbonate particles in the film. The resulting laminate may define a water vapor transmission rate of from about 1000 to about 5000 g/m$^2$/24 hours or more.

Examples of suitable breathable materials for the outer cover 20 are also described in U.S. Pat. No. 5,879,341 issued Mar. 9, 1999 to Odorzynski et al. and entitled "ABSORBENT ARTICLE HAVING A BREATHABILITY GRADIENT"; U.S. Pat. No. 5,843,056 issued Dec. 1, 1988, to Good et al. and entitled "ABSORBENT ARTICLE HAVING A COMPOSITE BREATHABLE OUTER COVER"; and U.S. Pat. No. 5,855,999 issued Jan. 5, 1999 to McCormack et al. and entitled "BREATHABLE, CLOTH-LIKE FILM/NONWOVEN COMPOSITE", the disclosures of which are herein incorporated by reference.

The absorbent material 36 of the diaper 20, as representatively illustrated in FIGS. 1 and 2, may suitably comprise a matrix of hydrophilic fibers, such as a web of cellulosic fluff, mixed with particles of a high-absorbency material commonly known as superabsorbent material. In a particular embodiment, the absorbent material 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent material 36 to better contain and absorb body exudates. The concentration of the superabsorbent particles may also vary through the thickness of the absorbent material 36. Alternatively, the absorbent material 36 may comprise a laminate of fibrous webs and superabsorbent material or other suitable means of maintaining a superabsorbent material in a localized area.

The absorbent material 36 may have any of a number of shapes. For example, the absorbent material may be rectangular, I-shaped, or T-shaped. It is generally preferred that the absorbent material 36 be narrower in the crotch area than in the front or rear portions of the diaper 20. The size and the absorbent capacity of the absorbent material 36 should be compatible with the size of the intended wearer and the liquid loading imparted by the intended use of the absorbent product.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent material include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present disclosure are SANWET IM 3900 polymer available from Hoechst Celanese located in Portsmouth, Va., and DOW DRYTECH 2035LD polymer available from Dow Chemical Company located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent material in an amount of from about 5 to about 90 weight percent based on a total weight of the absorbent material 36.

Optionally, a substantially hydrophilic tissue wrapsheet (not shown) may be employed to help maintain the integrity of the airlaid fibrous structure of the absorbent material 36. The tissue wrapsheet is typically placed about the absorbent material over at least the two major facing surfaces thereof and composed of an absorbent cellulosic material, such as creped wadding or a high wet-strength tissue. In one aspect of the disclosure, the tissue wrapsheet can be configured to provide a wicking layer, which helps to rapidly distribute liquid over the mass of absorbent fibers comprising the absorbent material. In another aspect of the disclosure, the wrapsheet material on one side of the absorbent fibrous mass may be bonded to the wrapsheet located on the opposite side of the fibrous mass.

The inner liner 34, as representatively illustrated in FIGS. 1 and 2, suitably presents a bodyfacing surface which is compliant, soft feeling, and non-irritating to the wearer's skin. Further, the inner liner 34 may be less hydrophilic than the absorbent material 36, to present a relatively dry surface to the wearer, and may be sufficiently porous to be liquid permeable, permitting liquid to readily penetrate through its thickness. A suitable inner liner 34 may be manufactured from a wide selection of web materials, such as porous foams, reticulated foams, apertured plastic films, natural fibers (i.e., wood or cotton fibers), synthetic fibers (i.e., polyester or polypropylene fibers), or a combination of natural and synthetic fibers. The inner liner 34 is suitably employed to help isolate the wearer's skin from liquids held in the absorbent material 36.

Various woven and nonwoven fabrics can be used for the inner liner 34. For example, the inner liner 34 may be composed of a meltblown or spunbonded web of polyolefin fibers. The inner liner 34 may also be a bonded-carded web composed of natural and/or synthetic fibers. The inner liner 34 may be composed of a substantially hydrophobic material, and the hydrophobic material may, optionally, be treated with a surfactant, a wetting agent, or otherwise processed to impart a desired level of wettability and hydrophilicity.

In a particular embodiment, the inner liner 34 comprises a nonwoven, spunbond, polypropylene fabric composed of about 1-3 denier fibers formed into a web having a basis weight of about 20 grams per square meter and a density of about 0.13 gram per cubic centimeter. The fabric may be surface treated with about 0.3 weight percent of a surfactant mixture, which contains a mixture of AHCOVEL Base N-62 and GLUCOPON 220UP surfactant in a 3:1 ratio based on a total weight of the surfactant mixture. The AHCOVEL Base N-62 is purchased from Uniqema (New Castle, Del.) and includes a blend of hydrogenated ethoxylated castor oil and sorbitan monooleate in a 55:45 weight ratio. The GLUCOPON 220UP is purchased from Cognis Corporation and includes alkyl polyglycoside. The surfactant may be applied by any conventional means, such as spraying, printing, brush coating, or the like. The surfactant may be applied to the entire inner liner 34, or may be selectively applied to particular sections of the inner liner 34, such as the medial section along the longitudinal centerline of the diaper, to provide greater wettability of such sections.

Now referring to FIG. 2, the translucent window is formed by first applying a clearing composition (not shown) to the inner surface 100 of the liquid impermeable outer cover 32; that is, the surface 100 of the outer cover 32 in direct contact with the absorbent material 36, and then applying a water dispersible ink (not shown) over the clearing composition. Specifically, in one embodiment, the clearing composition is a clearing varnish.

To form a suitable translucent window in the absorbent products of the present disclosure, the clearing composition is a varnish having at least one of specific molecular weights and/or various other functional properties, including specific melting temperatures (also referred to as melting point) and melting indices. Furthermore, in one particularly preferred embodiment, the clearing varnish should have wetting properties and surface tension such as to be able to be wetted during application onto the inner surface of the liquid impermeable outercover and penetrate into the porous structure of the liquid permeable inner layer, thereby allowing an even spread of the varnish onto the inner surface of the liquid impermeable outercover.

Typically, in one particularly preferred embodiment, the clearing varnish is a varnish having a number average molecular weight of from about 150 to about 1500. More suitably, the clearing varnish has a number average molecular weight of from about 200 to about 1000, and even more suitably, from about 220 to about 500.

In another embodiment, the clearing varnish for use in the clearing composition has a melting point of from about 65° C. to about 95° C. More suitably, the clearing varnish has a melting point of from about 70° C. to about 90° C. Even more suitably, the clearing varnish has a melting point of from about 75° C. to about 85° C.

The clearing varnish of the clearing composition of another embodiment may suitably have a melt index of from about 300 to about 1500. More suitably, the clearing varnish has a melt index of from about 350 to about 1200, and even more suitably, from about 400 to about 900.

In one particularly preferred embodiment, the clearing varnish comprises epoxidized soybean oil. Specifically, the clearing varnish of this embodiment, has a number average molecular weight of from about 200 to about 500, and is a viscous liquid at room temperature. One particularly suitable epoxidized soybean oil-containing clearing varnish is Paraplex G-62, commercially available from ITW Dynatec (Hendersonville, Tenn.), which has a viscosity at 25° C. of approximately 407 centipoise.

In an alternative embodiment, the clearing varnish for use in the clearing composition is an ethylene-vinyl acetate copolymer. Typically, the ethylene-vinyl acetate copolymer has from about 25% (by total weight copolymer) to abut 30% (by total weight copolymer) vinyl acetate. More suitably, the ethylene-vinyl acetate copolymer has about 28% (by total weight copolymer) vinyl acetate.

When used as the clearing varnish, the ethylene-vinyl acetate copolymer suitably has a melting point of from about 70° C. to about 90° C. and a melt index of from about 300 to about 1200. Specific examples of particularly preferred ethylene-vinyl acetate copolymers for use in the clearing composition are commercially available Elvax® 205W and Elvax® 210W (both available from E.I. du Pont de Nemours and Co., Wilmington, Del.). Elvax® 205W has a melting temperature of about 80° C. and a melt index of about 800. Elvax® 210W has a melting temperature of about 82° C. and a melt index of about 400.

In yet another alternative embodiment, the clearing varnish is a tallow-based oleamide. Typically, the tallow-based oleamide has a melting temperature of about 65° C. to about 85° C. More suitably, the tallow-based oleamide has a melting temperature of about 70° C. to about 80° C. One particularly preferred tallow-based oleamide is commercially available Armoslip® CP (available from Akzo Nobel, The Netherlands), a 9-ocetadecnamide, having the chemical formula $C_{18}H_{35}ON$. Typically, Armoslip® CP has a number average molecular weight of about 282.5 and a melting temperature of from about 72° C. to about 76° C.

One additional suitable clearing varnish is polyethylene glycol distearate, such as polyethylene glycol 400 distearate, commercially available from Ruger Chemical Co., Inc., Linden, N.J. Polyethylene glycol 400 distearate is produced using polyethylene glycol having a number average molecular weight of approximately 400. Furthermore, polyethylene glycol 400 distearate has a melting temperature of approximately 36° C.

While described separately, it should be understood by one skilled in the art that the clearing varnish can include one of the above-described compositions or can include a combination of the compositions without departing from the present disclosure.

Typically, the clearing varnish is disposed on the inner surface of the liquid impermeable outer cover of the absorbent product. More specifically, the liquid impermeable outer cover of the absorbent product includes the clearing varnish in an amount of from about 10 grams per square meter ($g/m^2$) to about 75 $g/m^2$. More suitably, the liquid impermeable outer cover includes from about 20 $g/m^2$ to about 50 $g/m^2$ of clearing varnish.

In an alternative embodiment, as described above, the clearing composition is a paraffin wax. Paraffin waxes suitable for the clearing composition typically have the generic chemical formula: $C_nH_{2n+2}$. Suitably, the paraffin wax has a melting point of from about 45° C. to about 70° C. and a number average molecular weight of from about 350 to about 450.

Similar to the clearing varnish, when paraffin wax is used in the clearing composition, the paraffin wax is disposed on the inner surface 100 of the liquid impermeable outer cover 32 of the absorbent product. More specifically, the liquid impermeable outer cover 32 of the absorbent product includes the paraffin wax in an amount of from about 10 grams per square meter ($g/m^2$) to about 75 $g/m^2$. More suitably, the liquid impermeable outer cover 32 includes from about 20 $g/m^2$ to about 50 $g/m^2$ of paraffin wax.

In addition to the clearing varnish and/or paraffin wax, the clearing composition for use on the absorbent product includes a water dispersible ink. As stated above, disappearing or fading graphics preferably are printed with ink that disappears or fades when wetted, or when heated, or when exposed to the atmosphere for a period of time. The amount of fluid and/or heat and/or time needed to make the ink disappear should be less than the amount of fluid and/or heat generated during a normal insult of urine, which may depend upon the size of the absorbent product (and likewise the size of the wearer).

Suitable water dispersible inks or dyes useful in printing the fading graphics of the present disclosure are those that disappear or fade when subjected to liquid and/or heat. Preferably, the water dispersible ink(s) used to print graphics is a water dispersible ink of the type disclosed in U.S. Pat. No. 4,022,211. Examples of water soluble ink formulations include a water-soluble polyvinyl alcohol diluted with water, combined with appropriate coloring agents. For instance, a blue water soluble ink could be formulated from a 50% solution of Cascorex EA 9065, a polyvinyl alcohol from Borden Adhesives, diluted with distilled water with the addition of 0.1% by weight of GAF Neptune Blue BRA dye. Another suitable formulation is a solution comprised of 50% water, 50% of water-soluble polyvinyl alcohol (Cascorex EA 9065, about 8% solids from Borden Chemical Company), colored with a tissue dye (Sky Blue 6BX from E.I. DuPont Company) in the amount of 0.5% by weight. Coloring agents used in these formulations could be substituted with others, to produce different colors. Examples of other suitable coloring agents include: Pontamine Turquoise 8 GLP (a direct blue dye), Bond yellow CS (a direct yellow dye), DuPont Red 8BLX (a direct red dye), Rhodamine B Extra (a basic red dye), and Paper Blue R (a direct dye) all available from E.I. DuPont Company; and EASTACRYL dark red dye available from Eastman Kodak Company. Coloring agents also could be added in different concentrations to produce different color intensities. Those skilled in the art are capable of designing and manufacturing a suitable ink for use in the invention, using the guidelines provided herein.

In one embodiment the water dispersible ink includes the specific combination of isopropyl alcohol, methyl alcohol, and an organic volatile. Examples of such particularly preferred water dispersible inks are commercially available AquaDestruct inks bearing designations ESMSW5834784 (permanent blue), ESB507045SW (disappearing blue), ESMFW4834783 (permanent red), and ESMFW4834731 (disappearing red), all available from Sun Chemical Ink, Northlake, Ill.

Typically, the absorbent product includes water dispersible ink in a weight ratio of clearing composition to water dispersible ink of from about 10:90 to about 90:10. More suitably, the absorbent product includes water dispersible ink in a weight ratio of clearing composition to water dispersible ink of from about 25:75 to about 75:25, and even more preferably, about 50:50.

In addition to the absorbent products, the present disclosure is directed to making the absorbent products having a translucent window for viewing a fading graphic. Generally, the method comprises: applying a clearing composition onto an inner surface of a liquid impermeable outer cover of an absorbent product; and printing a water dispersible ink over the clearing composition. Specifically, the clearing composition (i.e., clearing varnish and/or paraffin wax) form a translucent window on the liquid impermeable outer cover of the absorbent product. The water dispersible ink is then applied over the translucent window.

The clearing composition can be applied to the outer cover of the absorbent product using any method known to one skilled in the art. For example, when a clearing varnish such as described above is the clearing composition, the clearing varnish can be applied using a method selected from the group consisting of flexographic printing, gravure printing, cell rolling, slot coating, stamping, and extrusion coating.

Slot coating: The clearing varnish is metered through a slot in a printing head directly onto the inner surface of the liquid impermeable outer cover.

Direct gravure printing: The clearing varnish is in small cells in a gravure roll. The inner surface of the outer cover comes into direct contact with the gravure roll and the clearing varnish in the cells is transferred onto the outer cover.

Offset gravure printing with reverse roll transfer: Similar to the direct gravure technique except the gravure roll transfers the clearing varnish to a second roll. This second roll then comes into contact with the inner surface of the outer cover to transfer clearing varnish onto the outer cover.

Forward and reverse cell rolling (also known as transfer roll coating): This consists of a stack of rolls which transfers the clearing varnish from one roll to the next for metering purposes. The final roll comes into contact with the inner surface of the outer cover. The moving direction of the interface and the rotation of the final roll determine whether the process is a forward process or a reverse process.

Extrusion coating: This technique is similar to the slot die technique except that the clearing varnish is a solid at room temperature. The clearing varnish is heated to melting temperature in the print head and metered as a liquid through the slot directly onto the inner surface of the outer cover. Upon cooling, the clearing varnish becomes a solid again.

Flexographic printing: The clearing varnish is transferred onto a raised patterned surface of a roll. This patterned roll then contacts the inner surface of the liquid impermeable outer cover to transfer the clearing varnish onto the outer cover.

Other suitable methods of applying the clearing varnish can include spraying, chemical deposition, and the like.

In one embodiment, the clearing varnish is heated to a temperature of at least about 93° C. prior to being applied to the inner surface of the liquid impermeable outer cover of the absorbent product. More suitably, the clearing varnish is heated to a temperature of from about 105° C. to about 180° C.

When the clearing composition includes a paraffin wax as described more fully above, the paraffin wax is applied by heating the wax and applying the paraffin wax onto an inner surface of the liquid impermeable outer cover. More particularly, the paraffin wax is heated to a temperature of from about 90° C. to about 150° C. In one embodiment, the paraffin wax is heated prior to being applied to the outer cover. In another embodiment, the paraffin wax is applied to the outer cover and then the outer cover and the wax are heated.

Specifically, in one embodiment the liquid impermeable outer cover is a polymer film as described above and the paraffin wax is applied to the polymer film. Once applied, both the film and wax are introduced onto a hot surface to allow the paraffin wax to melt onto the inner surface of the film to form the translucent window.

While described herein as being applied to the outer cover of the absorbent product, it should be understood that the clearing composition and water dispersible ink can be applied onto any of the components of the absorbent product using techniques known in the art. For example, the clearing composition and water dispersible ink can be applied directly to the absorbent core or to an intermediate web.

As noted above, the translucent windows formed using the above-described methods allow for a clearer view of a wetness indicator such as the water dispersible ink to determine when an insult of the absorbent product has occurred (or any other condition of the product and/or user as described above). Specifically, the clarity of the translucent windows as produced using the methods of the present disclosure can be determined using the BYK Gardner Haze-gard Plus and the method used in accordance with this test, and the color value and opacity of the windows can be determined using the BYK Gardner Color-guide sphere and the methods used in accordance with these tests.

Having described the invention in detail, it will be apparent that modifications and variations are possible without departing from the scope of the disclosure defined in the appended claims.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above products without departing from the scope of the disclosure, it is intended that all matter contained in the above description and shown in the accompanying drawings shall be interpreted as illustrative and not in a limiting sense.

What is claimed is:

1. An absorbent product comprising:
   a liquid impermeable outer cover comprising a clearing varnish capable of forming a translucent window and a water dispersible ink applied over the translucent window, the clearing varnish having at least one of a number average molecular weight of from about 150 to about 1500, a melting point of from about 65° C. to about 95° C., and a melt index of from about 300 to about 1500;
   an absorbent material; and
   a liquid permeable inner layer, wherein the outer cover comprises from about 10 g/m$^2$ to about 75 g/m$^2$ clearing varnish.

2. The absorbent product as set forth in claim 1 wherein the clearing varnish has a number average molecular weight of from about 200 to about 1000.

3. The absorbent product as set forth in claim 1 wherein the clearing varnish has a melting point of from about 70° C. to about 90° C.

4. The absorbent product as set forth in claim 1 wherein the clearing varnish has a melt index of from about 350 to about 1200.

5. The absorbent product as set forth in claim 1 wherein the water dispersible ink comprises isopropyl alcohol, methyl alcohol, and an organic volatile.

6. The absorbent product as set forth in claim 1 wherein the clearing varnish is selected from the group consisting of an ethylene-vinyl acetate copolymer, a tallow-based oleamide, a polyethylene glycol distearate, and combinations thereof.

7. The absorbent product as set forth in claim 6 wherein the clearing varnish is 9-ocetadecenamide.

8. The absorbent product as set forth in claim 1 wherein the clearing varnish comprises epoxidized soybean oil.

9. An absorbent product comprising:
   a liquid impermeable outer cover comprising a clearing varnish capable of forming a translucent window and a water dispersible ink applied over the translucent window, the clearing varnish being selected from the group consisting of an epoxidized soybean oil, an ethylene-vinyl acetate copolymer, a tallow-based oleamide, a polyethylene glycol distearate, and combinations thereof, and the water dispersible ink comprising isopropyl alcohol, methyl alcohol, and an organic volatile;
   an absorbent material; and
   a liquid permeable inner layer, wherein the outer cover comprises from about 10 g/m$^2$ to about 75 g/m$^2$ clearing varnish.

10. A method of making an absorbent product comprising a translucent window for viewing a fading graphic, the method comprising:

applying from about 10 g/m$^2$ to about 75 g/m$^2$ clearing varnish onto an inner surface of a liquid impermeable outer cover to form a translucent window, the clearing varnish having at least one of a number average molecular weight of from about 150 to about 1500, a melting point of from about 65° C. to about 95° C., and a melt index of from about 300 to about 1500; and printing a water dispersible ink over the translucent window.

11. The method as set forth in claim 10 wherein the clearing varnish comprises epoxidized soybean oil.

12. The method as set forth in claim 10 wherein the clearing varnish is selected from the group consisting of an ethylene-vinyl acetate copolymer, a tallow-based oleamide, a polyethylene glycol distearate, and combinations thereof.

13. The method as set forth in claim 12 wherein the clearing varnish is 9-ocetadecenamide.

14. The method as set forth in claim 10 wherein the water dispersible ink comprises isopropyl alcohol, methyl alcohol, and an organic volatile.

15. The method as set forth in claim 10 wherein the clearing varnish is heated prior to applying the clearing varnish to the inner surface of the liquid impermeable outer cover.

* * * * *